(12) United States Patent
Heaney et al.

(10) Patent No.: US 7,906,128 B2
(45) Date of Patent: Mar. 15, 2011

(54) USE OF NEURONAL SODIUM CHANNEL ANTAGONISTS FOR THE CONTROL OF ECTOPARASITES IN HOMEOTHERMIC ANIMALS

(75) Inventors: Kathleen Heaney, Yardley, PA (US); Susan J. Dunney, Titusville, NJ (US); Douglas Rugg, Lebanon, NJ (US)

(73) Assignee: Wyeth LLC, Madison, NJ (US)

( * ) Notice: Subject to any disclaimer, the term of this patent is extended or adjusted under 35 U.S.C. 154(b) by 1165 days.

(21) Appl. No.: 10/684,995

(22) Filed: Oct. 14, 2003

(65) Prior Publication Data
US 2004/0116419 A1 Jun. 17, 2004

(51) Int. Cl.
*A01N 25/04* (2006.01)

(52) U.S. Cl. ........ 424/405; 424/406; 514/590; 514/617; 514/639; 514/715

(58) Field of Classification Search ......... None
See application file for complete search history.

(56) References Cited

U.S. PATENT DOCUMENTS

| | | | |
|---|---|---|---|
| 4,560,553 A | 12/1985 | Zupan | |
| 4,710,512 A | 12/1987 | Webb | |
| 5,116,850 A | 5/1992 | Stevenson | |
| 5,304,573 A | 4/1994 | Hino et al. | |
| 5,324,837 A | 6/1994 | Renga et al. | |
| 5,462,938 A | 10/1995 | Annus et al. | |
| 5,543,573 A | 8/1996 | Takagi et al. | |
| 5,708,170 A | 1/1998 | Annis et al. | |
| 5,965,137 A * | 10/1999 | Petrus | 424/756 |
| 5,968,990 A | 10/1999 | Jon et al. | |
| 6,955,818 B1 * | 10/2005 | Hacket et al. | 424/405 |
| 2004/0122075 A1 | 6/2004 | Chiarello et al. | |
| 2006/0078585 A1 * | 4/2006 | Sabnis et al. | 424/405 |

FOREIGN PATENT DOCUMENTS

| | | |
|---|---|---|
| EP | 0036138 B1 | 8/1985 |
| EP | 1 334 661 A1 | 8/2003 |
| EP | 1413201 A2 | 4/2004 |
| JP | 08 268994 A | 10/1996 |
| JP | 09 301947 A | 11/1997 |
| WO | WO 92/06076 | 4/1992 |
| WO | WO 96/10560 | 4/1996 |
| WO | 00/54591 * | 9/2000 |
| WO | WO 01/01781 A1 | 1/2001 |
| WO | WO 2006/002984 A1 | 1/2006 |
| WO | WO 2006/042099 A1 | 4/2006 |

OTHER PUBLICATIONS

Gregory T. Payne, et al., Pesticide Biochemistry and Physiology, "Structure-Activity Relationships for the Action of Dihydropyrazole Insecticides on Mouse Brain Sodium Channels," 60, 1998, pp. 177-185.

Keith D. Wing, et al., Archives of Insect Biochemistry and Physiology, "A Novel Oxadiazine Insecticide Is Bioactivated in Lepidopteran Larvae," 37, 1998, pp. 91-103.

Remington, Joseph P., "Remington: The Science and Practice of Pharmacy", 19th Edition, 1995 p. 1583.

Package Insert Frontline Top Spot® for Dogs, Merial Limited, purchased Jan. 31, 2008.

* cited by examiner

*Primary Examiner* — Neil Levy

(74) *Attorney, Agent, or Firm* — Joel Silver

(57) ABSTRACT

The present invention provides an effective method and composition for the prevention, amelioration or control of external parasites on a human or animal via the administration of a prophylactically, therapeutically or pharmaceutically effective amount of a neuronal sodium channel antagonist to a human or animal in need thereof.

10 Claims, No Drawings

USE OF NEURONAL SODIUM CHANNEL ANTAGONISTS FOR THE CONTROL OF ECTOPARASITES IN HOMEOTHERMIC ANIMALS

BACKGROUND OF THE INVENTION

Virtually all commercial and most companion animals are affected by ectoparasites, often resulting in clinical disease and subclinical conditions that adversely affect the animal. Insects such as Phthiraptera (lice) and Diptera (flies), are among the most economically important ectoparasites affecting animal production. Insects such as Siphonaptera (fleas) are pests to companion animals. Ticks and mites in the order Acarina are serious pests of both production and companion animals. Ectoparasitic infection and infestation seriously affect the economies of raising production animals and also are a source of great concern for companion animals. New economic methods and compositions for the prevention, treatment and control of ectoparasites in warm-blooded animals are constantly being sought.

SUMMARY OF THE INVENTION

The present invention comprises a method for the prevention, amelioration or control of ectoparasitic infection or infestation in a homeothermic animal which comprises administering to a homeothermic animal in need thereof a prophylactically, therapeutically or pharmaceutically effective amount of a neuronal sodium channel antagonist. The present invention further comprises a pharmaceutically acceptable carrier and an ectoparasiticidally effective amount of a neuronal sodium channel antagonist. The neuronal sodium channel antagonist used in the method and composition of this invention preferably is a compound of formula I, II or III

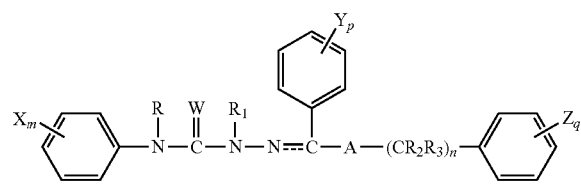

(I)

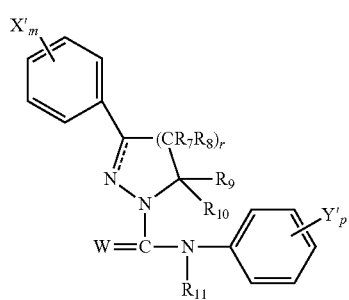

(II)

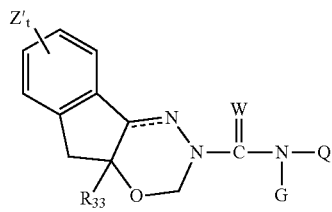

(III)

wherein
A is $CR_4R_5$ or $NR_6$;
W is O or S;
X, Y, Z, X', Y' and Z' are each independently H; halogen; OH; CN; $NO_2$; $C_1$-$C_6$alkyl optionally substituted with one or more halogen, $C_1$-$C_3$alkoxy, $C_1$-$C_3$haloalkoxy, $C_3$-$C_6$cycloalkyl, $C_2$-$C_6$alkenyloxy or sulfonyloxy groups;
$C_1$-$C_6$alkoxy optionally substituted with one or more halogen, $C_1$-$C_3$alkoxy or $C_3$-$C_6$cycloalkyl groups;
$C_1$-$C_6$alkoxycarbonyl, $C_3$-$C_6$cycloalkylcarbonyloxy, phenyl optionally substituted with one or more halogen, $C_1$-$C_4$alkyl, or $C_1$-$C_4$alkoxy groups;
aminocarbonyloxy optionally substituted with one or more $C_1$-$C_3$alkyl groups;
$C_1$-$C_6$alkoxycarbonyloxy; $C_1$-$C_6$alkylsulfonyloxy; $C_2$-$C_6$alkenyl; or $NR_{12}R_{13}$;
m, p and q are each independently an integer of 1, 2, 3, 4, or 5;
n is an integer of 0, 1 or 2;
r is an integer of 1 or 2;
t is an integer of 1, 2, 3 or 4;
R, $R_1$, $R_2$, $R_3$, $R_4$ and $R_5$ are each independently H or $C_1$-$C_4$alkyl;
$R_6$ is H, $C_1$-$C_6$alkyl, $C_1$-$C_6$haloalkyl, $C_1$-$C_6$alkoxyalkyl, $C_1$-$C_6$alkoxy, $C_1$-$C_6$haloalkoxy, $C_2$-$C_6$alkenyl, $C_2$-$C_6$alkynyl, $C_1$-$C_6$alkylcarbonyl, $C_1$-$C_6$alkoxycarbonyl, $C_1$-$C_6$alkylthio, or $C_1$-$C_6$haloalkylthio;
$R_7$ and $R_8$ are each independently H; halogen; $C_1$-$C_6$alkyl; $C_1$-$C_6$alkylcarbonyloxy; or phenyl optionally substituted with one or more halogen, CN, $NO_2$, $C_1$-$C_6$alkyl, $C_2$-$C_6$haloalkyl, $C_1$-$C_6$alkoxy or $C_1$-$C_6$haloalkoxy groups;
$R_9$ and $R_{10}$ are each independently H, or $C_1$-$C_4$alkyl;
$R_{11}$ is H, $C_1$-$C_6$alkyl, $C_1$-$C_6$haloalkyl, $C_1$-$C_4$alkylcarbonyl, $C_1$-$C_6$alkoxycarbonyl, or $C_1$-$C_6$haloalkoxycarbonyl;
$R_{12}$ and $R_{13}$ are each independently H or $C_1$-$C_6$alkyl;
G is H; $C_1$-$C_6$alkyl optionally substituted with one or more halogen, $C_1$-$C_4$alkoxy, $C_1$-$C_6$haloalkoxy, CN, $NO_2S(O)_uR_{14}$, $COR_{15}$, $CO_2R_{16}$, phenyl or $C_3$-$C_6$cycloalkyl groups;
$C_1$-$C_6$alkoxy; $C_1$-$C_6$haloalkoxy; CN; $NO_2$; $S(O)_uR_{17}$; $COR_{18}$; $CO_2R_{19}$; phenyl optionally substituted with one or more halogen, CN, $C_1$-$C_3$haloalkyl, or $C_1$-$C_3$haloalkoxy groups;
$C_3$-$C_6$cycloalkyl; or phenylthio;
Q is phenyl optionally substituted with one or more halogen, CN, SCN, $NO_2$, $S(O)_uR_{20}$, $C_1$-$C_4$alkyl, $C_1$-$C_4$haloalkyl, $C_1$-$C_4$alkoxyalkyl, $C_1$-$C_6$alkoxy, $C_1$-$C_6$haloalkoxy, or $NR_{21}R_{22}$ groups;
u is an integer of 0, 1 or 2;
$R_{14}$, $R_{15}$, $R_{16}$, $R_{18}$, $R_{19}$, $R_{21}$ and $R_{22}$ are each independently H or $C_1$-$C_6$alkyl;

$R_{17}$ and $R_{20}$ are each independently $C_1$-$C_6$alkyl or $C_1$-$C_6$haloalkyl;

$R_{33}$ is $CO_2R_{34}$;

$R_{34}$ is H, $C_1$-$C_6$alkyl, $C_1$-$C_6$haloalkyl, phenyl or halophenyl; and the dotted line configuration C≡≡≡N represents a double bond or a single bond;

or a compound of formula IV or V

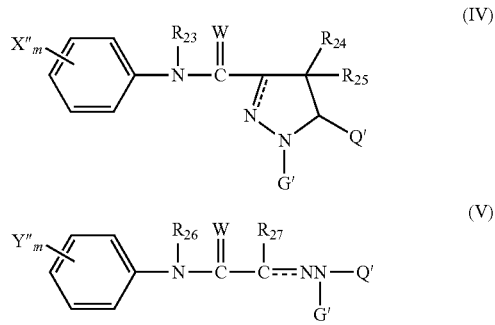

wherein

W is O or S;

X" and Y" are each independently H; halogen; CN; SCN; $C_1$-$C_6$alkyl optionally substituted with one or more halogen, $NO_2$, CN, $C_1$-$C_4$alkoxy, $C_1$-$C_4$alkylthio, phenyl, halophenyl, $C_1$-$C_4$alkylsulfonyl, $C_1$-$C_4$haloalkylsulfonyl, or $C_1$-$C_4$alkoxycarbonyl groups; $C_2$-$C_4$alkenyl; $C_2$-$C_4$haloalkenyl; $C_2$-$C_4$alkynyl; $C_2$-$C_4$haloalkynyl; $C_3$-$C_6$cycloalkyl; $C_3$-$C_6$halocycloalkyl; phenyl optionally substituted with one or more halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfonyl or $C_1$-$C_4$haloalkylsulfonyl groups; $C_1$-$C_4$alkylcarbonyl; $C_1$-$C_4$haloalkylcarbonyl; or $NR_{28}R_{29}$;

m is an integer of 1, 2, 3, 4 or 5;

G' is phenyl optionally substituted with one or more groups which may be the same or different selected from X";

a 5-membered heteroaromatic ring containing one or two heteroatoms selected from 0 or 1 oxygen, 0 or 1 sulfur and 0, 1 or 2 nitrogen atoms said 5-membered heteroaromatic ring being attached via carbon and being optionally substituted with one or more groups which may be the same or different selected from X"; or a 6-membered heteroaromatic ring containing one or two heteroatoms selected from 0 or 1 oxygen, 0 or 1 sulfur and 0, 1 or 2 nitrogen atoms said 6-membered heteroaromatic ring being attached via carbon and being optionally substituted with one or more groups which may be the same or different selected from X";

Q' is H; $C_1$-$C_6$alkyl optionally substituted with one or more halogen, CN, $C_1$-$C_3$alkoxy, $C_1$-$C_6$alkoxycarbonyl, or phenyl optionally substituted with one or more halogen, CN, $NO_2$, $C_1$-$C_4$alkyl, $C_1$-$C_4$haloalkyl, $C_1$-$C_4$alkylsulfonyl or $C_1$-$C_4$alkylsulfinyl groups; $C_2$-$C_6$alkenyl; $C_2$-$C_6$alkynyl; or phenyl optionally substituted with one to three groups, which may be the same or different, selected from X";

$R_{23}$, $R_{24}$, $R_{25}$, $R_{26}$, $R_{27}$, $R_{28}$ and $R_{29}$ are each independently H or $C_1$-$C_4$alkyl; and the dotted line configuration C≡≡≡N represents a double bond or a single bond;

or a stereoisomer thereof.

An object of this invention is to provide a method for the prevention, amelioration or control of ectoparasitic infection or infestation in a homeothermic animal which comprises administering to a homeothermic animal in need thereof a prophylactically, therapeutically or pharmaceutically effective amount of a neuronal sodium channel antagonist.

A further object of this invention is to provide a composition which comprises a pharmaceutically acceptable carrier and an ectoparasiticidally effective amount of a neuronal sodium channel antagonist.

It is also an object of this invention to provide an effective method for the prevention, treatment or control of ectoparasitic infection or infestation in animals and humans.

It is another object of this invention to provide an ectoparasiticidal composition suitable for use on animals and humans.

Further objects, advantages and features of the invention will become apparent to those skilled in the art from the detailed description set forth below, and from the appended claims.

DETAILED DESCRIPTION OF THE INVENTION

Ecotoparasiticidal infection and infestation are a constant problem in animal husbandry and in the care and raising of companion animals. Surprisingly, it has now been found that ectoparasites may be prevented or controlled in homeothermic animals by administration to said animals of a prophylactically, therapeutically or pharmaceutically effective amount of a neuronal sodium channel antagonist. The term "neuronal sodium channel antagonist" as used herein designates a compound which is capable of preventing the ability of a neuron cell to transfer sodium ions across the cell membrane. A neuron cell thus affected is unable to fire, resulting in paralysis, and ultimately mortality in the target pest. Descriptions of neuronal sodium channel antagonists and their mode of action may be found in Pesticide Biochemistry and Physiology, 60: 177-185 or Archives of Insect Biochemistry and Physiology, 37: 91-103.

Neuronal sodium channel antagonists have been available in the art, and include compounds such as those described in U.S. Pat. Nos. 5,543,573; 5,708,170; 5,324,837 and 5,462,938, the descriptions of which are hereby incorporated by reference. Exemplary of the neuronal sodium channel antagonist compounds useful in the anti-ectoparasitic method and composition of this invention are those compounds having one of the following the structural formulae:

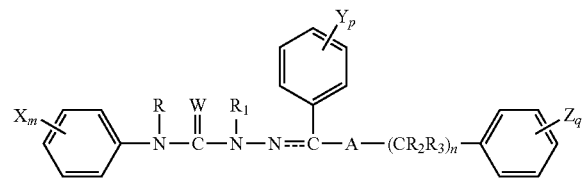

-continued

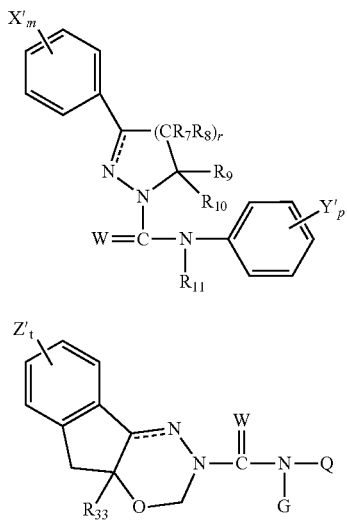

wherein
A is $CR_4R_5$ or $NR_6$;
W is O or S;
X, Y, Z, X', Y' and Z' are each independently H; halogen; OH; CN; $NO_2$; $C_1$-$C_6$alkyl optionally
  substituted with one or more halogen, $C_1$-$C_3$alkoxy, $C_1$-$C_3$haloalkoxy, $C_3$-$C_6$cycloalkyl, $C_2$-$C_6$alkenyloxy or sulfonyloxy groups;
  $C_1$-$C_6$alkoxy optionally substituted with one or more halogen, $C_1$-$C_3$alkoxy or $C_3$-$C_6$cycloalkyl groups;
  $C_1$-$C_6$alkoxycarbonyl, $C_3$-$C_6$cycloalkylcarbonyloxy, phenyl optionally substituted with one or more halogen, $C_1$-$C_4$alkyl, or $C_1$-$C_4$alkoxy groups;
  aminocarbonyloxy optionally substituted with one or more $C_1$-$C_3$alkyl groups;
  $C_1$-$C_6$alkoxycarbonyloxy; $C_1$-$C_6$alkylsulfonyloxy; $C_2$-$C_6$alkenyl; or $NR_{12}R_{13}$;
m, p and q are each independently an integer of 1, 2, 3, 4, or 5;
n is an integer of 0, 1 or 2;
r is an integer of 1 or 2;
t is an integer of 1, 2, 3 or 4;
R, $R_1$, $R_2$, $R_3$, $R_4$ and $R_5$ are each independently H or $C_1$-$C_4$alkyl;
$R_6$ is H, $C_1$-$C_6$alkyl, $C_1$-$C_6$haloalkyl, $C_1$-$C_6$alkoxyalkyl, $C_1$-$C_6$alkoxy, $C_1$-$C_6$haloalkoxy, $C_2$-$C_6$alkenyl, $C_2$-$C_6$alkynyl, $C_1$-$C_6$alkylcarbonyl, $C_1$-$C_6$alkoxycarbonyl, $C_1$-$C_6$alkylthio, or $C_1$-$C_6$haloalkylthio;
$R_7$ and $R_8$ are each independently H; halogen; $C_1$-$C_6$alkyl; $C_1$-$C_6$alkylcarbonyloxy; or phenyl optionally substituted with one or more halogen, CN, $NO_2$, $C_1$-$C_6$alkyl, $C_2$-$C_6$haloalkyl, $C_1$-$C_6$alkoxy or $C_1$-$C_6$haloalkoxy groups;
$R_9$ and $R_{10}$ are each independently H, or $C_1$-$C_4$alkyl;
$R_{11}$ is H, $C_1$-$C_6$alkyl, $C_1$-$C_6$haloalkyl, $C_1$-$C_4$alkylcarbonyl, $C_1$-$C_6$alkoxycarbonyl, or $C_1$-$C_6$haloalkoxycarbonyl;
$R_{12}$ and $R_{13}$ are each independently H or $C_1$-$C_6$alkyl;
G is H; $C_1$-$C_6$alkyl optionally substituted with one or more halogen, $C_1$-$C_4$alkoxy, $C_1$-$C_6$haloalkoxy, CN, $NO_2S(O)_uR_{14}$, $COR_{15}$, $CO_2R_{16}$, phenyl or $C_3$-$C_6$cycloalkyl groups;
$C_1$-$C_6$alkoxy; $C_1$-$C_6$haloalkoxy; CN; $NO_2$; $S(O)_uR_{17}$; $COR_{18}$; $CO_2R_{19}$; phenyl optionally substituted with one or more halogen, CN, $C_1$-$C_3$haloalkyl, or $C_1$-$C_3$haloalkoxy groups;
$C_3$-$C_6$cycloalkyl; or phenylthio;
Q is phenyl optionally substituted with one or more halogen, CN, SCN, $NO_2$, $S(O)_uR_{20}$, $C_1$-$C_4$alkyl, $C_1$-$C_4$haloalkyl, $C_1$-$C_4$alkoxyalkyl, $C_1$-$C_6$alkoxy, $C_1$-$C_6$haloalkoxy, or $NR_{21}R_{22}$ groups;
u is an integer of 0, 1 or 2;
$R_{14}$, $R_{15}$, $R_{16}$, $R_{18}$, $R_{19}$, $R_{21}$ and $R_{22}$ are each independently H or $C_1$-$C_6$alkyl;
$R_{17}$ and $R_{20}$ are each independently $C_1$-$C_6$alkyl or $C_1$-$C_6$haloalkyl;
$R_{33}$ is $CO_2R_{34}$;
$R_{34}$ is H, $C_1$-$C_6$alkyl, $C_1$-$C_6$haloalkyl, phenyl or halophenyl; and the dotted line configuration C⚌N represents a
double bond or a single bond (i.e. C—N or C═N); or
a stereoisomer thereof.

The term haloalkyl as used in the specification and claims designates alkyl group $C_xH_{2x+1}$ having 1 to 2x+1 halogen atoms which may be the same or different. Similarly, the terms haloalkenyl, haloalkynyl, haloalkoxy, halophenyl, and the like designate mono- to perhalogen substitution wherein the halogens may be the same or different. The term halogen designates Cl, Br, I or F.

Preferred neuronal sodium channel antagonists suitable for use in this invention are those compounds of formula I, II and III wherein the dotted line configuration C⚌N represents a double bond.

More preferred neuronal sodium channel antagonists suitable for use in the inventive method and composition are those compounds of formula I and formula III in which the dotted line configuration C⚌N represents a double bond.

Particularly preferred neuronal sodium channel antagonists are those compounds of formula I wherein A is $CH_2$; W is O; X is 4-$OCF_3$; Y is 3-$CF_3$; Z is 4-CN; n is 0; m, p and q are each 1; R and $R_1$ are each H; and the dotted line configuration C⚌N represents a double bond; or a stereoisomer thereof.

Further neuronal sodium channel antagonist compounds include those described in U.S. Pat. Nos. 5,116,850 and 5,304,573, the descriptions of which are hereby incorporated by reference. Exemplary of further neuronal sodium channel antagonist compounds suitable for use in the method of the invention are those compounds having the structural formula IV or V:

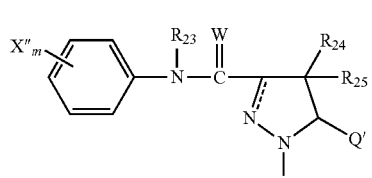

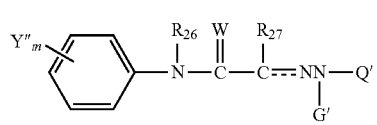

wherein
W is O or S;
X' and Y' are each independently H; halogen; CN; SCN; $C_1$-$C_6$alkyl optionally substituted with one or more halogen, $NO_2$, CN, $C_1$-$C_4$alkoxy, $C_1$-$C_4$alkylthio, phenyl, halophenyl, $C_1$-$C_4$alkylsulfonyl, $C_1$-$C_4$haloalkylsulfonyl, or $C_1$-$C_4$alkoxycarbonyl groups;

$C_2$-$C_4$alkenyl; $C_2$-$C_4$haloalkenyl; $C_2$-$C_4$alkynyl; $C_2$-$C_4$haloalkynyl; $C_3$-$C_6$cycloalkyl; $C_3$-$C_6$halocycloalkyl; phenyl optionally substituted with one or more halogen, CN, $NO_2$, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkylsulfonyl or $C_1$-$C_4$haloalkylsulfonyl groups;

$C_1$-$C_4$alkylcarbonyl; $C_1$-$C_4$haloalkylcarbonyl; or $NR_{28}R_{29}$;

m is an integer of 1, 2, 3, 4 or 5;

G is phenyl optionally substituted with one or more groups which may be the same or different selected from X";

a 5-membered heteroaromatic ring containing one or two heteroatoms selected from 0 or 1 oxygen, 0 or 1 sulfur and 0, 1 or 2 nitrogen atoms said 5-membered heteroaromatic ring being attached via carbon and being optionally substituted with one or more groups which may be the same or different selected from X"; or a 6-membered heteroaromatic ring containing one or two heteroatoms selected from 0 or 1 oxygen, 0 or 1 sulfur and 0, 1 or 2 nitrogen atoms said 6-membered heteroaromatic ring being attached via carbon and being optionally substituted with one or more groups which may be the same or different selected from X";

Q' is H; $C_1$-$C_6$alkyl optionally substituted with one or more halogen, CN, $C_1$-$C_3$alkoxy, $C_1$-$C_6$alkoxycarbonyl, or phenyl optionally substituted with one or more halogen, CN, $NO_2$, $C_1$-$C_4$alkyl, $C_1$-$C_4$haloalkyl, $C_1$-$C_4$alkylsulfonyl or $C_1$-$C_4$alkylsulfinyl groups;

$C_2$-$C_6$alkenyl; $C_2$-$C_6$alkynyl; or phenyl optionally substituted with one to three groups, which may be the same or different, selected from X";

$R_{23}$, $R_{24}$, $R_{25}$, $R_{26}$, $R_{27}$, $R_{28}$ and $R_{29}$ are each independently H or $C_1$-$C_4$alkyl; and the dotted line configuration C$=\!=\!=$N represents a double bond or a single bond; or a stereoisomer thereof.

Further preferred neuronal sodium channel antagonist compounds of the invention are those compounds of formula IV or V wherein the dotted line configuration C$=\!=\!=$N represents a double bond.

In another preferred embodiment of this invention, the neuronal sodium channel antagonist compounds are those compounds of formula IV or V wherein W is O; X" and Y" are each independently H or $C_1$-$C_6$haloalkyl; m is 1; $R_{23}$, $R_{24}$, $R_{25}$, $R_{26}$ and $R_{27}$ are each H; G is phenyl optionally substituted with one or more halogen atoms; Q is halophenyl or $C_1$-$C_4$alkyl optionally substituted with one phenyl or halophenyl group; and the dotted line configuration C$=\!=\!=$N represents a double bond; or a stereoisomer thereof.

Each of the compounds of formulae I, II, III, IV and V include assymetric centers which may be represented in the stereoisomeric R-form or S-form. The present invention includes methods and compositions comprising R-isomers, S-isomers, or mixtures thereof in any ratio, of the compounds of formulae I, II, III, IV and V. For compounds of formula III, the S-isomeric form is preferred.

Advantageously, it has now been found that a neuronal sodium channel antagonist may be used to effectively control, prevent or ameliorate infection and infestation of ectoparasites on homeothermic animals. Important agronomic and companion animals such as cattle, sheep, horses, goats, pigs, llamas, camels, water buffalo, donkeys, rabbits, fallow deer, reindeer, minks, chinchillas, ferrets, racoons, chickens, geese, turkeys, ducks, dogs, cats, rats, or the like are prone to attack and infestation by biting and sucking ectoparasitic insects such as Diptera, Pthiraptera or Siphonaptera, and parasitic Acari such as ticks and mites. In particular, Diptera: Muscidae such as *Musca autumnalis* (face flies), *Haemtobia irritans* (horn flies) *Stomoxys calcitrans* (stable flies), heel flies, tsetse flies, blow flies or the like are breeders of filth and vectors of disease and are serious pests of animals such as cattle, horses and sheep. Further, Diptera: Hippoboscidae (louse flies) such as *Melophagus ovinus* (sheep ked), which is a serious parasite of sheep are problematic in animal production.

Among the Phthiraptera families known to be parasites of animals are: Trichodectidae such as *Bovicola bovis* (important cattle-biting louse), *B. ovis* (sheep-biting louse) or *B. equi* (horsebiting louse); Haematopinidae such as *Haematopinus suis* (hog louse), or *H. asini* (horse sucking louse); Linognathidae such as *Linognathus stenopsis* (goat sucking louse) or *L. vituli* (long-nosed cattle louse); or the like.

One of the Siphonaptera families known to infest companion animals is Pulicidae such as Archaeopsyllinae (cat and dog fleas), Spilopsyllinae (rabbit fleas), or the like.

From the Order Acarina, some of the ticks and mites known to infest production and companion animals are, *Argas* spp., *Ornithodoros* spp., *Dermanyssus gallinae*, *Boophilus* spp., *Rhipicephalus* spp., *Amblyomma* spp., *Dermacentor* spp., *Hyalomma* spp., *Ixodes* spp., *Psoroptes* spp., *Chorioptes* spp., *Sarcoptes* spp., *Cheyletiella* spp., and the like.

Protection of homeothermic animals from the infestation of ectoparasites, particularly of the orders Diptera, Phthiraptera, Siphonaptera or Acarina may be provided or enhanced by the application or administration of a prophylactically, therapeutically or pharmaceutically effective amount of a neuronal sodium channel antagonist compound.

In the practice of this invention, an antagonist compound may be applied to the animal as a dip, spray, pour-on, spot-on, ear tag, collar, medallion, backrubber, oiler, dustbag, powder, lotion, shampoo, parenteral injection, oral dosage, or the like, preferably by a topical application such as a pour-on, spray, dip or spot-on.

The effective amount of the neuronal sodium channel antagonist compound to be used in the method of invention will vary according to the specific compound used, the mode of application, the identity of the ectoparasite to be controlled, the degree of infestation, the extent of the ectoparasitic insect population, the nature of the target host, the weather conditions, or other factors known to those in the art.

Effective dosages may range from about 0.1 mg/kg to about 100 mg/kg, preferably about 1.0 mg/kg to about 50 mg/kg. Naturally, quantities of greater than effective amounts of said antagonist compound may be administered, but are not required for the protection of the target animal from the ectoparasite.

Accordingly, the present invention also provides a composition which comprises a pharmaceutically acceptable carrier and an ectoparasiticidally effective amount of a neuronal sodium channel antagonist. Preferred embodiments of the composition of the invention include an aqueous dip for animals such as cattle, sheep, goats or the like, as well as a wettable powder, emulsifiable concentrate, and aqueous flowable formulation, each of which may be dispersed in a suitable solvent and applied as sprays to the fur or hide of the animals. Such sprays usually contain about 0.1 ppm to about 5000 ppm and preferably about 0.5 ppm to about 1000 ppm of the active neuronal sodium channel antagonist compound.

In another preferred embodiment of the invention, the neuronal sodium channel antagonist is formulated as a pour-on or spot-on formulation and applied to the backs of the animals to be treated, such as cattle, sheep or companion animals, to protect them against infestation by arthropod ectoparasites. The pour-on or spot-on compositions of this invention are suitably prepared by, dissolving, suspending or emulsifying the antagonist compound in a suitable nontoxic pharmaceutically acceptable diluent. The diluent must be compatible with the antagonist and should not be a source of irritation or damage to the animal's skin or hair. Such diluents include monohydric and polyhydric alcohols, vegetable oils, spreading oils, aliphatic and aromatic hydrocarbons, lower alkyl ketones, esters, fatty acids and other diluents known in the art.

One preferred type of pour-on or spot-on formulation of this invention comprises about 0.5% to about 30% by weight of the neuronal sodium channel antagonist, about 0.5 to about 30% by weight of a spreading oil, about 30% to about 60% by weight of an aliphatic or aromatic hydrocarbon, an alcohol, a glycol, a lower alkyl ketone, or a mixture thereof, and 0% to about 20% by weight of a vegetable or mineral oil or a mixture thereof.

Another preferred type of pour-on or spot-on formulation comprises about 45% by weight of xylene, about 25% by weight of cyclohexanone, about 15% by weight of a neuronal sodium channel antagonist compound, 10% by weight of corn oil or mineral oil or a mixture thereof, and about 5% by weight of other pharmaceutically acceptable diluents such as surfactants, spreading agent, antifoam agents or the like. Among the preferred spreading agents or oils that can be utilized in pour-on formulations of this invention are fatty acids, fatty acid esters, triglycerides and fatty alcohols including: isopropyl myristate, capryl/caproic acid esters of saturated ($C_{12}$-$C_{18}$) fatty alcohols with waxy fatty acid esters, isopropyl palmitate and the like.

Alcohols, glycols and ketones useful in the practice of this invention include: ethyl alcohol, isopropyl alcohol, propylene glycol, dipropylene glycol, benzyl alcohol, dipropylene glycol monoethyl ether, cyclohexanone, methylethyl ketone, methylisobutyl ketone, N-butoxybutylethoxyethanol, and the like. Vegetable oils that may be utilized in the formulations of this invention include: corn oil, olive oil, peanut oil, sunflower oil, cottonseed oil, soybean oil, and the like.

Aromatic hydrocarbons that can be used as solvents in the formulation and method of this invention include: xylene, toluene, and the like. Other suitable solvents include but are not limited to hexane, dimethyl sulfoxide, and isopropyl myristate, and solvents similar to each of these. Combinations of solvents also may be used. Those skilled in the art will readily be able to identify suitable solvent systems. Suitable solvents are those which dissolve one or more of the other ingredients of the formulation, do not poison or harm the animal being treated, and do not negatively affect the activity of the active ingredients.

Surfactants may also be utilized in the formulations of this invention, if desired. These include any suitable surfactants known in the art.

Formulations of this invention may contain one or more active ingredients in addition to a neuronal sodium channel antagonist. These additional ingredients may include an effective amount of an insect growth regulator (IGR) known in the art, including but not limited to chitin synthesis inhibitors such as the benzoylphenylureas (e.g., diflubenzuron, flufenoxuron, teflubenzuron, lufenuron, novaluron, fluazuron, and the like), and juvenile hormone mimics such as methoprene, hydroprene, pyriproxyfen, and fenoxycarb, and the like. The amount needed to be effective will, of course, vary depending on the ectoparasite target and the particular IGR, as well as the method and conditions of application of the formulation. Those skilled in the art will readily be able to determine an effective amount for each case without undue experimentation.

Formulations of this invention may also contain an effective amount of one or more ectoparasiticides known in the art in addition to a neuronal sodium channel antagonist, including but not limited to: amidine insecticides/acaricides such as amitraz; pyrethroid/acaricides insecticides such as permethrin, cypermethrin and alpha-cypermethrin; phenylpyrazole insecticides/acaricides such as fipronil; organophosphorus insecticides such as chlorfenvinphos, diazinon, malathion, and terbufos; imidacloprid; nitepyram; carbamate insecticides; and the like. The amount of insecticide needed to be effective will, of course, vary depending on the parasite target and the particular insecticide/acaricide, as well as the method and conditions of application of the formulation. Those skilled in the art will readily be able to determine an effective amount for each case without undue experimentation.

Formulations of this invention may also contain an effective amount of one or more macrocyclic lactone (ML) parasiticides known in the art in addition to a neuronal sodium channel antagonist, including but not limited to: avermectins such as abamectin, doramectin, ivermectin, eprinomectin, selamectin, avermectin, and the like, and milbemycins such as moxidectin, milbemycin oxime, and the like. The amount of ML needed to be effective will, of course, vary depending on the parasite target and the particular ML, as well as the method and conditions of application of the formulation. Those skilled in the art will readily be able to determine an effective amount for each case without undue experimentation.

The method of this invention includes the application of formulations of this invention, including those containing more than one active ingredient such as insecticides and/or IGRs.

In order to present a more clear understanding of the invention, the following specific examples are set forth below. These examples are merely illustrative and are not to be understood as limiting the scope or underlying principles of the invention in any way. Indeed, various modifications of the invention, in addition to those illustrated and described herein, will become apparent to persons skilled in the art from the following examples and the foregoing description. Such modifications are also intended to fall within the scope of the appended claims.

Example 1

Comparative Evaluation of the Efficacy of a Neuronal Sodium Channel Antagonist Against Blowfly In this evaluation, filter paper discs are treated with an acetone solution of test compound and allowed to dry. Bovine serum and newly emerged larvae of blowfly, *Lucilia sericata*, are added to the treated filter paper and mortality is assessed at 24 h and 48 h and the lethal concentrations ($LC_{50}$ and $LC_{99}$) are calculated using regression analysis described in POLO-PC, a user's guide to probit or logit analysis, LeOra Software, Berkeley, Calif., 1987. The results are shown in Table I.

TABLE I

| Test Compound | 24 h | | 48 h | |
|---|---|---|---|---|
| | $LC_{50}$ (μg/mL) | $LC_{99}$ (μg/mL) | $LC_{50}$ (μg/mL) | $LC_{99}$ (μg/mL) |
| $A^1$ | 0.40 | 1.27 | 0.27 | 0.71 |
| Standard[2] | 0.10 | 0.40 | 0.07 | 0.30 |

[1]Compound A = formula of neuronal sodium channel antagonist

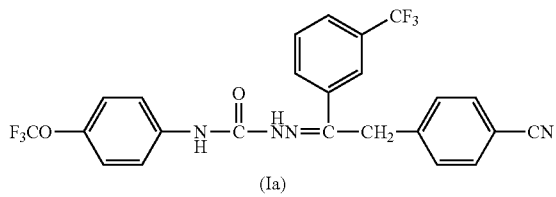

(Ia)

[2]Standard = fipronil

Example 2

Comparative Evaluation of the Efficacy of a Neuronal Sodium Channel Antagonist Against Adult Fleas In this evaluation twelve beagles are each infested with 100 unfed adult fleas. Each dog is assessed for its ability to retain fleas by a comb count taken 24 hours post infestation. The dogs are blocked by these flea counts and randomly assigned to one of four treatment groups. Test compounds are applied as a full body spray of a 0.40% (wt/vol) solution of test compound in a mixture of 1% Miglyol in N-methyl-2-pyrrolidinone. One day prior to treatment each dog is infested with 100 fleas and one day post treatment the dogs are comb counted to check for knockdown efficacy. The dogs were subsequently re-infested with fleas and comb counted 24 hours later at weekly intervals. The data are averaged and shown in Table II.

TABLE II

Percent Efficacy Relative to Nontreated Control for Beagles Treated with a Topical Formulation of Compound A

| Treatment | % Efficacy (DAT) | | | | | | | | | |
|---|---|---|---|---|---|---|---|---|---|---|
| | 1 | 7 | 14 | 21 | 28 | 35 | 42 | 49 | 56 | 62 |
| Compound $A^1$ (20 mg/kg body wt.) | 100 | 99.7 | 99.6 | 100 | 100 | 100 | 99.5 | 97.8 | 92.6 | 64.2 |
| Standard[2] (14.5 mg/kg body wt.) | 100 | 100 | 100 | 100 | 100 | 100 | 100 | 100 | 100 | 99.5 |
| Placebo (Blank solvent mixture) | 100 | 56.0 | 28.2 | 27.1 | 0.0 | 17.9 | 12.2 | 40.0 | 0.8 | 0.0 |
| Control (No treatment) | 0 | 0 | 0 | 0 | 0 | 0 | 0 | 0 | 0 | 0 |

[1]Compound A = formula of neuronal sodium channel antagonist
[2]Standard = fipronil

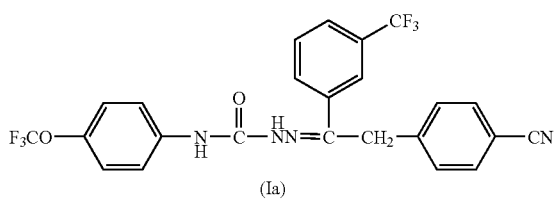

(Ia)

Example 3

Comparative Evaluation of the Efficacy of a Neuronal Sodium Channel Antagonist Combined with Another Active Ingredient Against Adult Fleas Four formulations containing the neuronal sodium channel inhibitor designated as Compound A in Example 1, three of which also contain another active ingredient, were tested and compared to other formulations, as is shown in Table Ill.

Table III

Geometric Mean Flea Counts and Percent Efficacy (bolded) Relative to Nontreated Control for Beagles Treated with Topical Formulations of Compound a Combined with Amitraz or Permethrin

| Treatment (mg/kg body weight) on Day 0 | Days After Treatment | | | | |
|---|---|---|---|---|---|
|  | 1 | 7 | 14 | 21 | 28 |
| Compound A 20% w/v (40), amitraz 10% w/v (20), IPM 20% w/v, cineole 10% w/v in DEET | 1.4 98.2 | 0.0 100 | 0.3 99.7 | 0.3 99.7 | 0.0 100 |
| Compound A 20% w/v (40), amitraz 10% w/v (20), in IPM | 0.3 99.7 | 0.3 99.7 | 0.6 99.3 | 0.4 99.4 | 1.2 98.5 |
| Compound A 20% w/v (40), permethrin 20% w/v (40), in DEET | 6.0 92.4 | 0.0 100 | 0.0 100 | 0.0 100 | 0.0 100 |
| Compound A 20% w/v (40) in DEET | 19.3 75.8 | 1.1 98.6 | 0.7 99.1 | 0.3 99.7 | 2.1 97.3 |
| Permethrin 20% w/v (40) in DEET | 6.7 91.6 | 0.3 99.7 | 0.0 100 | 0.0 100 | 0.9 98.8 |
| Advantage ® (10% w/v, 10 mg/kg body weight imidacloprid) | 0.0 100 | 0.0 100 | 1.1 98.6 | 0.8 98.9 | 13.2 82.8 |
| Frontline ® (10% w/v, 6.7 mg/kg body weight fipronil) | 1.5 98.2 | 0.3 99.7 | 0.0 100 | 0.0 100 | 0.0 100 |
| Nontreated Control | 79.8 | 77.6 | 79.6 | 75.8 | 76.8 |

IPM = isopropyl myristate; DEET = diethyl toluamide

Example 4

Comparative Evaluation of the Efficacy of a Neuronal Sodium Channel Antagonist Combined with Another Active Ingredient Against Ticks The formulations used in Example 3 were used against ticks with the results shown below in Table IV.

TABLE IV

Geometric Mean Tick Counts and Percent Efficacy (bolded) Relative to Nontreated Control for Beagles Treated with Topical Formulations of Compound A Combined with Amitraz or Permethrin

| Treatment (mg/kg body weight) on Day 0 | Days After Treatment | | | | |
|---|---|---|---|---|---|
|  | 1 | 7 | 14 | 21 | 28 |
| Compound A 20% w/v (40), amitraz 10% w/v (20), IPM 20% w/v, cineole 10% w/v in DEET | 1.2 96.2 | 0.0 100 | 0.4 98.3 | 0.4 98.3 | 0.4 98.4 |
| Compound A 20% w/v (40), amitraz 10% w/v (20), in IPM | 2.5 91.9 | 0.3 99.2 | 0.8 96.9 | 0.8 96.9 | 3.8 86.3 |
| Compound A 20% w/v (40), permethrin 20% w/v (40), in DEET | 7.0 77.7 | 2.5 92.1 | 2.5 90.6 | 5.9 77.3 | 12.4 54.8 |
| Compound A 20% w/v (40) in DEET | 10.1 66.8 | 6.5 79.1 | 6.5 75.3 | 12.8 50.7 | 9.7 64.7 |
| Permethrin 20% w/v (40) in DEET | 5.5 82.2 | 1.1 96.5 | 1.3 95.1 | 2.6 90.2 | 8.2 70.1 |
| Advantage ® (10% w/v, 10 mg/kg body weight imidacloprid) | 3.2 89.7 | 3.3 89.3 | 6.0 77.4 | 9.2 64.9 | 11.9 56.8 |
| Frontline ® (10% w/v, 6.7 mg/kg body weight fipronil) | 3.6 88.3 | 0.4 98.6 | 0.8 96.9 | 0.6 97.7 | 1.7 93.8 |
| Nontreated Control | 30.6 | 31.0 | 26.3 | 26.1 | 27.5 |

IPM = isopropyl myristate; DEET = diethyl toluamide

What is claimed is:

1. An ectoparisiticidal composition which comprises a pharmaceutically acceptable carrier and about 20% w/v of a neuronal sodium channel antagonist which is a compound of the formula:

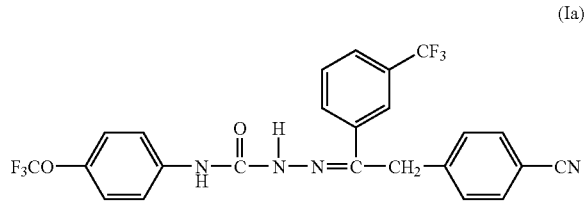

(Ia)

together with about 10% w/v of amitraz, about 20% w/v of isopropyl myristate and about 10% cineole in diethyl toluamide, wherein each w/v % indicates weight in relation to the total volume of the composition.

2. An ectoparisiticidal composition which comprises a pharmaceutically acceptable carrier and about 20% w/v of a neuronal sodium channel antagonist which is a compound of the formula:

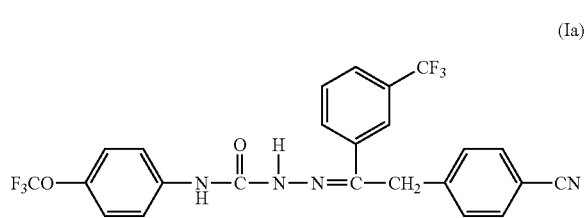

(Ia)

together with about 10% w/v of amitraz, in isopropyl myristate, wherein each w/v % indicates weight in relation to the total volume of the composition.

3. An ectoparisiticidal composition which comprises a pharmaceutically acceptable carrier and about 30% w/v of:
amitraz and a neuronal sodium channel antagonist which is a compound of the formula:

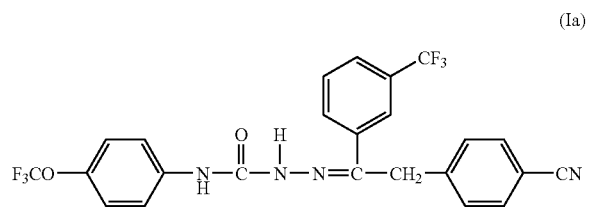

(Ia)

wherein the about 30% w/v is the combined weight of amitraz and the neuronal sodium channel antagonist in relation to the total volume of the composition.

4. The ectoparisiticidal composition of claim 3, further comprising diethyl toluamide.

5. The ectoparasiticidal composition of claim 3, further comprising cineole.

6. The ectoparasiticidal composition of claim 5, wherein the cineole is present at about 10% w/v in relation to the total volume of the composition.

7. The ectoparasiticidal composition of claim 3, wherein the carrier comprises a lower alkyl ketone or an ester.

8. The ectoparasiticidal composition of claim 7, wherein the lower alkyl ketone or the ester is present at about 30% to about 60% w/v in relation to the total volume of the composition.

9. The ectoparasiticidal composition of claim 3, wherein the carrier comprises a spreading agent.

10. The ectoparasiticidal composition of claim 3, wherein the spreading agent is isopropyl myristate.

* * * * *